US010285652B2

(12) United States Patent
Hosoda et al.

(10) Patent No.: US 10,285,652 B2
(45) Date of Patent: May 14, 2019

(54) TENDENCY DISCRIMINATION DEVICE, TASK EXECUTION ASSISTING DEVICE, TENDENCY DISCRIMINATION COMPUTER PROGRAM, AND TASK EXECUTION ASSISTING COMPUTER PROGRAM

(71) Applicant: ADVANCED TELECOMMUNICATIONS RESEARCH INSTITUTE INTERNATIONAL, Soraku-gun, Kyoto (JP)

(72) Inventors: Chihiro Hosoda, Soraku-gun (JP); Takashi Hanakawa, Tokyo (JP); Rieko Osu, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 344 days.

(21) Appl. No.: 14/650,121

(22) PCT Filed: Dec. 5, 2013

(86) PCT No.: PCT/JP2013/082722
§ 371 (c)(1),
(2) Date: Jun. 5, 2015

(87) PCT Pub. No.: WO2014/088073
PCT Pub. Date: Jun. 12, 2014

(65) Prior Publication Data
US 2015/0313551 A1 Nov. 5, 2015

(30) Foreign Application Priority Data
Dec. 7, 2012 (JP) ................................ 2012-268648

(51) Int. Cl.
*A61B 5/00* (2006.01)
*A61B 5/055* (2006.01)
(Continued)

(52) U.S. Cl.
CPC .......... *A61B 5/7267* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 6,820,037 B2 * 11/2004 Simon ...................... A61B 5/16
702/182
7,294,107 B2 * 11/2007 Simon ...................... A61B 5/16
434/236
(Continued)

FOREIGN PATENT DOCUMENTS

JP 2005-503196 A 2/2005
JP 2006-64880 A 3/2006
(Continued)

OTHER PUBLICATIONS

Dyrba et al., "Combining DTI and MRI for the Automated Detection of Alzheimer's Disease Using a Large European Multicenter Dataset". MBIA 2012, LNCS 7509, pp. 18-28, 2012 (Oct. 2012, P.-T. Yap et al. Eds.).*
(Continued)

*Primary Examiner* — Katherine L Fernandez
*Assistant Examiner* — Yi-Shan Yang
(74) *Attorney, Agent, or Firm* — Birch, Stewart, Kolasch & Birch, LLP

(57) ABSTRACT

A tendency discrimination device includes a discriminator to objectively discriminate a tendency of a person to be tested,
(Continued)

based on brain information obtained by magnetic resonance imaging (MRI). In the generation of the discriminator, a gray matter volume and a diffusion anisotropy degree are calculated for a frontal pole of each of multiple test subjects as a region of interest, and machine learning is performed on the relationship of the information obtained by classifying results of a test for discriminating the tendencies of the multiple test subjects, to gray matter volumes and diffusion anisotropy degrees obtained by MRI for each of the multiple test subjects.

18 Claims, 10 Drawing Sheets

(51) Int. Cl.
  *A61B 5/16* (2006.01)
  *G09B 7/00* (2006.01)
  *G09B 7/02* (2006.01)
  *G09B 23/28* (2006.01)
  *G01R 33/563* (2006.01)

(52) U.S. Cl.
  CPC .................. *A61B 5/16* (2013.01); *G09B 7/00* (2013.01); *G09B 7/02* (2013.01); *G09B 23/28* (2013.01); *A61B 5/165* (2013.01); *A61B 5/167* (2013.01); *A61B 5/168* (2013.01); *A61B 2576/026* (2013.01); *G01R 33/56341* (2013.01)

(56) References Cited

U.S. PATENT DOCUMENTS

2002/0103429 A1* 8/2002 deCharms .............. A61B 5/055
                                                    600/410
2011/0004092 A1    1/2011  Kato
2013/0178733 A1    7/2013  Langleben

FOREIGN PATENT DOCUMENTS

| JP | 2008-178546 A | 8/2008 |
| JP | 2009-72451 A | 4/2009 |
| JP | 2011-150408 A | 8/2011 |
| JP | 2011-206462 A | 10/2011 |
| WO | WO 2009/005013 A1 | 1/2009 |

OTHER PUBLICATIONS

Grahn et al., "Common Neural Recruitment across Diverse Sustained Attention Tasks". PLoS ONE 2012 7(11) (Nov. 2012), e49556, pp. 1-10.*

NeuroTrax, "MindstreamsTM Cognitive Health Assessment". Version 2.1, May 2003.*

Stonnington et al., "Predicting clinical scores from magnetic resonance scans in Alzheimer's disease". NeuroImage 51 (2010) 1405-1413.*

Cohen et al., "Connectivity-based segregation of the human striatum predicts personality characteristics," Nature Neuroscience, vol. 12, No. 1, Jan. 2009 (published online Nov. 23, 2008), pp. 32-34.

Laricchiuta et al., "Linking Novelty Seeking and Harm Avoidance Personality Traits to Cerebellar Volumes," Human Brain Mapping, vol. 35, 2014 (published online Sep. 11, 2012), pp. 285-296.

Sundgren et al., "Diffusion tensor imaging of the brain: review of clinical applications," Diagnostic Neuroradiology, vol. 46, 2004 (published online Apr. 21, 2004), pp. 339-350.

Van Schuerbeek et al., "Individual differences in local gray and white matter volumes reflect differences in temperament and character: A voxel-based morphometry study in healthy young females," Brain Research, vol. 1371, 2011 (available online Nov. 29, 2010), pp. 32-42.

* cited by examiner

TENDENCY DISCRIMINATION DEVICE, TASK EXECUTION ASSISTING DEVICE, TENDENCY DISCRIMINATION COMPUTER PROGRAM, AND TASK EXECUTION ASSISTING COMPUTER PROGRAM

TECHNICAL FIELD

The present invention relates to technologies of the discrimination of the tendency of a test subject and the task execution assistance based on the discrimination result, by using magnetic resonance imaging (MRI).

BACKGROUND OF THE INVENTION

Magnetic resonance imaging (MRI) is an imaging technique of magnetically exciting, by using RF signals at the Larmor frequency, the nuclear spin of a test object located in a static magnetic field, and recomposing an image from MR signals generated by the excitation. In the observation of a living body, signals of hydrogen nucleuses are mainly observed.

MRI technology has already had many applications in the medical diagnosis field. In addition, in the neuroimaging study using the MRI, there are some reports pointing out the relationship of the character tendency to the brain morphology and function in the structural MRI study (Non Patent Literature 1, Non Patent Literature 2, Non Patent Literature 3).

For example, Non Patent Literature 1 has reported a study about the correlation of the volumes of the gray matter and white matter in the frontal lobe and temporal lobe limbic system to the feature of the temperament and character. Further, Non Patent Literature 2 has reported that the volumes of the white matter and cortex in the cerebellum correlate with the feature of the temperament.

The temperament, for example according to the Cloninger theory, is considered at four dimensions: (1) Novelty seeking (NS, the inspiration of behavior), (2) Harm avoidance (HA, the suppression of behavior), (3) Reward Dependence (RD, the maintenance of behavior), and (4) Persistence (P, the fixation of behavior). The character is considered at three dimensions: (1) Self directedness (SD, autonomous individual), (2) Cooperativeness (C, the integral part of the human society), and (3) Self-transcendence (ST, the integral part of the universe).

Also, another technology different from the MRI technology has been proposed as a device for measuring the brain function. This technology estimate or predict the internal state of individuals such as the attention and the memory, using brain function measurement signals obtained from optical topography, and prevent and avoid human errors by detecting a state prone to human errors and by giving a warning (Patent Literature 1).

Thus, such a ergonomic application using the objective brain information for determining the tendency of the character of a person or for judging the current awareness state have been studied.

Furthermore, in the MRI technology described above, diffusion tensor imaging (DTI), developed in recent years, enables visualizations such as a stereoscopic visualization of the pyramidal tract, the corpus callosum and the like, and a visualization of the positional relationship between these and a nidus such as a tumor, based on the quantitative evaluation of the diffusion anisotropy closely associated with the density of the white matter, the degree of the degeneration and the like. The usefulness of this imaging method has already been demonstrated in clinical practice because it enables diagnosis which could not be done with other imaging method (Non Patent Literature 4).

The DTI images that the water-molecule diffusion direction is mainly restricted by the axis cylinder and myelin sheath of the nervous system, by using the MRI technology. The DTI quantifies the diffusion anisotropy, for example, with an index such as a FA (Fractional Anisotropy) value.

In such a DTI, there is a proposal about the setting method for an imaging target region in the DTI without depending on subjectivity or skill of a tester (Patent Literature 2).

In learning process, it is important to instruct a student according to the personality thereof. There has been a proposed system for discriminating the personality of the student by a written test, and for creating the information about an instruction guideline and a proceeding way of the learning (for example, Patent Literature 3). In the Patent Literature 3, the personality of a person is converted, using the answers to 80 questions, to five numerical factors, which are condensable property, receptive property, discriminable property, diffusible property, and preservative property and stress.

CITATION LIST

Patent Literature

Patent Literature 1: Japanese Unexamined Patent Application Publication No. 2011-150408
Patent Literature 2: Japanese Unexamined Patent Application Publication No. 2009-072451
Patent Literature 3: Japanese Unexamined Patent Application Publication No. 2006-64880

Non Patent Literature

Non Patent Literature 1: Van Schuerbeek P, Baeken C, De Raedt R, De Mey J, Luypaert R., "Individual differences in local gray and white matter volumes reflect differences in temperament and character: a voxel-based morphometry study in healthy young females," Brain Res. 2011 Jan. 31; 1371:32-42. Epub 2010 Nov. 29.
Non Patent Literature 2: Laricchiuta D, Petrosini L, Piras F, Macci E, Cutuli D, Chiapponi C, Cerasa A, Picerni E, Caltagirone C, Girardi P, Tamorri S M, Spalletta G., "Linking novelty seeking and harm avoidance personality traits to cerebellar volumes," Hum Brain Mapp. 2012 Sep. 11. doi: 10.1002/hbm.22174.
Non Patent Literature 3: Michael X Cohen, Jan-Christoph Schoene-Bakel, Christian E Egerl & Bernd Weber, "Connectivity-based segregation of the human striatum predicts personality characteristics," Nat Neurosci. 2009 January; 12(1):32-4. Epub 2008 Nov. 23.
Non Patent Literature 4: P. C. Sundgren et al., "Diffusion tensor imaging of the brain: review of clinical applications," Neuroradiology (2004) 46: 339-350.

SUMMARY OF INVENTION

Technical Problem

In the system described in the above Patent Literature 3, a certain level of objectivity can be expected. However, the system depends greatly on the experience of a question preparer in terms of the judgment of the character tendency and personality of a person, and the foundation, itself of the judgment is not objectively explained.

On the other hand, the MRI technology objectively acquires the structural and functional information about the brain. The development described above has been seen in recent years, but conventionally, it is not necessarily clear what relation there is between the information and the character tendency of a person, particularly, the tendency for learning.

Solution to Problem

This invention has been made to solve the above problems, and an object thereof is to provide a tendency discrimination device for objectively discriminating the tendency of a person to be tested based on brain information obtained by MRI.

Another object of this invention is to provide a task execution assisting device capable of presenting an appropriate task execution procedure based on the tendency of the person to be tested discriminated by the tendency decision device.

According to an aspect of this invention, a tendency discrimination device includes a storage unit and an arithmetic unit. The storage unit stores, in association with each of plurality of test subjects, data of an anatomical image and a diffusion weighted image obtained by magnetic resonance imaging for each of the test subjects, and classification information obtained by classifying results of a test for judging a tendency of each of the test subjects. The arithmetic unit executes a process for tendency discrimination, based on the information stored in the storage unit. The arithmetic unit calculates a gray matter volume and a diffusion anisotropy degree for a predetermined brain region as a region of interest, for each of the plurality of test subjects, based on the anatomical image and the diffusion weighted image. The arithmetic unit generates a discriminator by a machine learning of relationship of the classification information to the gray matter volume and the diffusion anisotropy degree. The discriminator outputs a tendency index of a person to be tested.

Further, a tendency discrimination device for discriminating a tendency of a person to be tested includes a discriminator and decision means. The discriminator is generated by a machine learning of relationship of information obtained by classifying results of a test to gray matter volumes and diffusion anisotropy degrees. The test is for judging tendencies of plurality of test subjects. The gray matter volumes and the diffusion anisotropy degrees are acquired for a predetermined brain region of the plurality of test subjects as a region of interest, based on anatomical images and diffusion weighted images obtained by magnetic resonance imaging. The decision means outputs a tendency index of the person to be tested, based on the discriminator, by using a gray matter volume and a diffusion anisotropy degree acquired for the predetermined brain region of the person to be tested as the region of interest based on an anatomical image and a diffusion weighted image obtained by magnetic resonance imaging.

Preferably, the tendency index is an index relevant to behavior sustainability of the person to be tested.

Preferably, the predetermined brain region is a frontal pole.

Preferably, the tendency is a tendency of the person to be tested for learning.

According to an alternative aspect of this invention, a task execution assisting device includes storage means, decision means, and assignment providing means. The storage means stores information about a discriminator generated by a machine learning of relationship of information obtained by classifying results of a test to gray matter volumes and diffusion anisotropy degrees. The test is for judging tendencies of plurality of test subjects. The gray matter volumes and the diffusion anisotropy degrees are acquired for a predetermined brain region of the plurality of test subjects as a region of interest, based on anatomical images and diffusion weighted images obtained by magnetic resonance imaging. The decision means outputs a tendency index of a person to be tested, based on the discriminator, by using a gray matter volume and a diffusion anisotropy degree acquired for the predetermined brain region of the person to be tested as the region of interest based on an anatomical image and a diffusion weighted image obtained by magnetic resonance imaging. The assignment providing means switches a presentation mode of assignments in a task program given to the person to be tested, depending on the tendency index.

Preferably, the tendency index is an index relevant to behavior sustainability of the person to be tested.

Preferably, the predetermined brain region is a frontal pole.

Preferably, for plurality of assignments composing the task program, a field of each of the assignments is classified in association with an interest of the person to be tested, or a category of each of the assignments is previously classified, and the assignment providing means, in progress of the task program, increase or decrease ratio of assignments in an interesting field, or increase or decrease frequency of switching of the category of the assignments, depending on the discriminated tendency of the person to be tested.

According to a further alternative aspect of this invention, a tendency discrimination computer program for making a computer execute discrimination of a tendency of a person to be tested makes the computer execute a step for acquiring a gray matter volume and a diffusion anisotropy degree for a predetermined brain region of the person to be tested as a region of interest, based on an anatomical image and a diffusion weighted image obtained by magnetic resonance imaging. The tendency discrimination computer program also makes the computer execute a step for outputting a tendency index of the person to be tested, based on a discriminant function generated by a machine learning of relationship of information obtained by classifying results of a test to gray matter volumes and diffusion anisotropy degrees. The test is for judging tendencies of plurality of test subjects. The gray matter volumes and the diffusion anisotropy degrees are acquired for the predetermined brain region of the plurality of test subjects as the region of interest, based on anatomical images and diffusion weighted images obtained by magnetic resonance imaging.

According to a further alternative aspect of this invention, a recording medium has the tendency discrimination computer program recorded therein.

According to a further alternative aspect of this invention, a task execution assisting computer program for making a computer execute a process of outputting a task program based on discrimination of a tendency of the person to be tested, the task program being given to the person to be tested, makes the computer execute four steps. The first step is to acquire a gray matter volume and a diffusion anisotropy degree for a predetermined brain region of the person to be tested as a region of interest, based on an anatomical image and a diffusion weighted image obtained by magnetic resonance imaging. The second step is to output a tendency index of the person to be tested, based on a discriminant function generated by a machine learning of relationship of information obtained by classifying results of a test to gray matter volumes and diffusion anisotropy degrees. The test is for judging tendencies of plurality of test subjects. The gray matter volumes and the diffusion anisotropy degrees are acquired for the predetermined brain region of the plurality of test subjects as the region of interest, based on anatomical images and diffusion weighted images obtained by magnetic resonance imaging. The fourth step is to switch and present a presentation mode of assignments in the task program given to the person to be tested, depending on the tendency index.

According to a further alternative aspect of this invention, a recording medium has the task execution assisting computer program recorded therein.

According to a further alternative aspect of this invention, a task execution assisting device includes brain information acquiring means and assignment providing means. The brain information acquiring means acquires a gray matter volume and a diffusion anisotropy degree for a predetermined brain region of a person to be tested as a region of interest, based on an anatomical image and a diffusion weighted image obtained by magnetic resonance imaging. The assignment providing means switches a mode depending on a tendency of the person to be tested. The mode is a presentation mode of assignments in a task program given to the person to be tested. The tendency of the person to be tested is discriminated by using brain information of the person to be tested, based on a discriminator. The discriminator is generated by a machine learning of relationship of information obtained by classifying results of a test to gray matter volumes and diffusion anisotropy degrees. The test is for judging tendencies of plurality of test subjects. The gray matter volumes and the diffusion anisotropy degrees are acquired for the predetermined brain region of the plurality of test subjects as the region of interest, based on anatomical images and diffusion weighted images obtained by magnetic resonance imaging.

Preferably, depending on the tendency of the person to be tested, the assignment providing means should switch a grade when giving a notice of evaluation of assignment achievement degree of the person to be tested, in the task program given to the person to be tested.

Advantageous Effects of Invention

According to the present invention, it is possible to objectively discriminate the tendency of a test subject, based on the brain information obtained by MRI.

Further, according to the present invention, it is possible to present an appropriate task execution procedure, based on the objectively discriminated tendency of the test subject.

DESCRIPTION OF EMBODIMENTS

Figure 1:
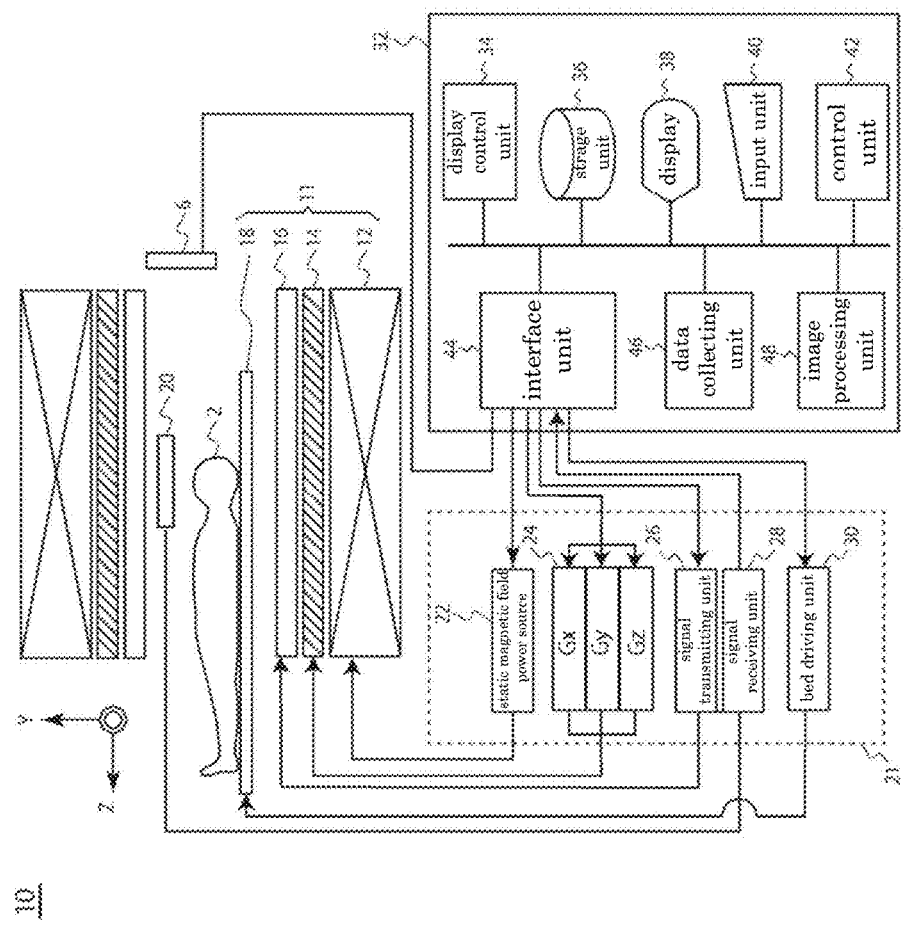
FIG. 1 is a block diagram showing the overall configuration of an MRI device 10.

Hereinafter, the configurations of a tendency discrimination device, a tendency discrimination program, and a task execution assisting device according to an embodiment of the present invention will be described with reference to the drawings. In the following embodiment, constituent elements or processing steps denoted by the same reference character are an identical or comparable one, and the description thereof will not be repeated unless it is needed.

First, as a premise to describe the configurations of the "tendency discrimination device and task execution assisting device" according to the embodiment, an "MRI device", which is a device for measuring the structure or function of the brain of a test subject, will be described.

Next, the "tendency" of a test subject or a person to be tested will be described, particularly, taking a "learning tendency" as an example, and the "task execution assisting device" will be described taking a "learning assisting device" as an example. However, the "tendency discrimination device and task execution assisting device" according to the embodiment are not limited thereto.

FIG. 1 is a block diagram showing the overall configuration of an MRI device 10.

As shown in FIG. 1, the MRI device 10 includes a magnetic field applying mechanism 11 for giving a controlled magnetic field to a region of interest of a test subject 2 and performing the irradiation with RF waves, a receiver coil 20 for receiving response waves (NMR signals) from the test subject 2 and outputting analog signals, a drive unit 21 for controlling the magnetic field given to the test subject 2 and controlling the transmission and reception of the RF waves, and a data processing unit 32 for setting a control sequence of the drive unit 21 and generating an image by processing various data signals.

Here, the Z-axis is the central axis of a cylindrical bore for placing the test subject 2. The X-axis is defined as the horizontal direction orthogonal to the Z-axis, and the Y-axis is defined as the vertical direction orthogonal to the Z-axis.

The MRI device 10 has such a configuration, and therefore, due to the static magnetic field applied by the magnetic field applying mechanism 11, the nuclear spin of atomic nucleuses configuring the test subject 2 is oriented in the magnetic field direction (Z-axis), and a precession is performed at the Larmor frequency specific to the atomic nucleus, such that the magnetic field direction is the axis.

Then, by the irradiation with RF pulses having the same frequency as the Larmor frequency, the atoms resonate, absorb energy, and are excited, so that the nuclear magnetic resonance phenomenon (NMR phenomenon) occurs. When the RF pulse irradiation is stopped after the resonance, electromagnetic waves (NMR signals) having the same frequency as the Larmor frequency are output in the relaxation process that the atoms release the energy and return to the original steady state.

The receiver coil 20 receives the output NMR signals as the response waves from the test subject 2, and the data processing unit 32 images the region of interest of the test subject 2.

The magnetic field applying mechanism 11 includes a static magnetic field generating coil 12, a gradient magnetic field generating coil 14, a RF irradiating unit 16, and a bed 18 for placing the test subject 2 in the bore.

The drive unit 21 includes a static magnetic field power source 22, a gradient magnetic field power source 24, a signal transmitting unit 26, a signal receiving unit 28, and a bed driving unit 30 for moving the bed 18 to any position in the Z-axis direction.

The data processing unit 32 includes an input unit 40 for receiving a variety of operations and information inputs from an operator (not illustrated), a display unit 38 for performing the screen display of a variety of images and a variety of information relevant to the region of interest of the test subject 2, a storage unit 36 for storing programs, control parameters, image data (such as a three-dimensional model image) and other electronic data for executing a variety of processes, a control unit 42 for controlling the operation of each function unit such as the generation of the control sequence for driving the drive unit 21, an interface unit 44 for transmitting and receiving of a variety of signals by the drive unit 21, a data collecting unit 46 for collecting the data composed of a group of NMR signals derived from the region of interest, and an image processing unit 48 for forming an image based on the data of the NMR signals.

The data processing unit 32 can be a dedicated computer. Alternatively, it can be a general computer for executing a function to make each function unit operate and for performing a designated calculation, a data process, and the control sequence generation, based on a program installed in the storage unit 36.

In the static magnetic field generating coil 12, a helical coil wound around the Z-axis generates induction magnetic field by the electric current supplied from the static magnetic field power source 22, and generates the static magnetic field in the Z-axis direction in the bore. The region of interest of the test subject 2 is set to a region that is high in the uniformity of the static magnetic field generated in the bore. In more detail, the static magnetic field generating coil 12, for example, is composed of four air core coils. These coils generate a uniform magnetic field in the interior by the combination of them, and gives an orientation to the spin of predetermined atomic nucleuses, more particularly hydrogen nucleuses, in the body of the test subject 2.

The gradient magnetic field generating coil 14, composed of an X coil, a Y coil, and a Z coil (not illustrated), is provided on the inner circumferential surface of the static magnetic field generating coil 12 having a cylindrical shape.

These X coil, Y coil, and Z coil perform the switching among the X-axis direction, the Y-axis direction, and the Z-axis direction in order, and therewith, superimpose gradient magnetic fields on the uniform magnetic field in the bore to give intensity gradients to the static magnetic field. In exciting, the Z coil limits a resonance plane by inclining the magnetic field intensity to the Z-direction. On applying the magnetic field in the Z direction, the Y coil adds a short-time gradient, and adds a phase modulation, proportional to the Y-coordinate, to a detection signal (phase encoding). Subsequently, the X coil adds a gradient at the time of acquiring the data, and gives a frequency modulation, proportional to the X-coordinate, to the detection signal (frequency encoding).

The transmitting unit 24 outputs different pulse signals to the X coil, the Y coil and the Z coil respectively, in accordance with the control sequence, and thereby, the switching of the gradient magnetic field to be superimposed is achieved. Thus, it is possible to specify a position in the test subject 2 where the NMR phenomenon occurs, and to obtain the positional information on the three-dimensional coordinates necessary for forming the image of the test subject 2.

The RF irradiating unit 16 irradiates radio frequency pulses (RF pulses) to the region of interest of the test subject 2, based on high frequency signals transmitted from the signal transmitting unit 33 in accordance with the control sequence. Although, in FIG. 1, the RF irradiating unit 16 is incorporated in the magnetic field applying mechanism 110, it may be provided on the bed 18 or may be integrated with the receiver coil 20.

The receiver coil 20 detects the response waves (NMR signals) from the test subject 2. The receiver coil 20 is disposed close to the test subject 2 so as to detect the NMR signals at a high sensitivity.

Here, when the electromagnetic waves of the NMR signals cut across the coil wire, a weak electric current is generated in the receiver coil 20, due to electromagnetic induction. The weak electric current is amplified and converted from analog signals into digital signals in the signal receiving unit 28, and then sent to the data processing unit 32.

That is, when a high frequency electromagnetic field with a resonance frequency is applied through the RF irradiating unit 16 to the test subject 2, in the state in which the Z-axis gradient magnetic field has been added to the static magnetic field, predetermined atomic nucleuses, which is for example hydrogen nucleuses, are selectively excited, and start to resonate. The predetermined atomic nucleuses at the portion meeting the resonance condition (for example, a sectional layer of the test subject 2 with a predetermined thickness) are excited, and the spins rotate simultaneously. When the excitation pulse is stopped, the electromagnetic waves radiated by the rotating spins, in turn, induce signals in the receiver coil 20, and the signals are detected for a while. By using the signals, a tissue containing the predetermined atoms in the body of the test subject 2 is observed. Then, the X and Y gradient magnetic fields are added, and the signals are detected to determine the transmission position of the signals.

Based on the data stored in the storage unit 36, the image processing unit 48 measures the detection signals while giving the excitation signals repeatedly, restores the resonance frequency for the X-coordinate by a first-time Fourier transform calculation, reproduces the Y-coordinate by a second-time Fourier transform calculation to obtain an image, and displays a corresponding image on the display unit 38.

(Region of Interest in Brain Observation)

The "tendency discrimination device and learning assisting device" according to the embodiment utilize the data obtained from the frontal pole of the brain as the region of interest (ROI), in an anatomical image and a diffusion weighted image measured by the MRI device. However, the region of interest may be another region of the brain, if it allows the procedure of the tendency discrimination to be experimentally confirmed in a way described below.

Figures 2A, 2B:
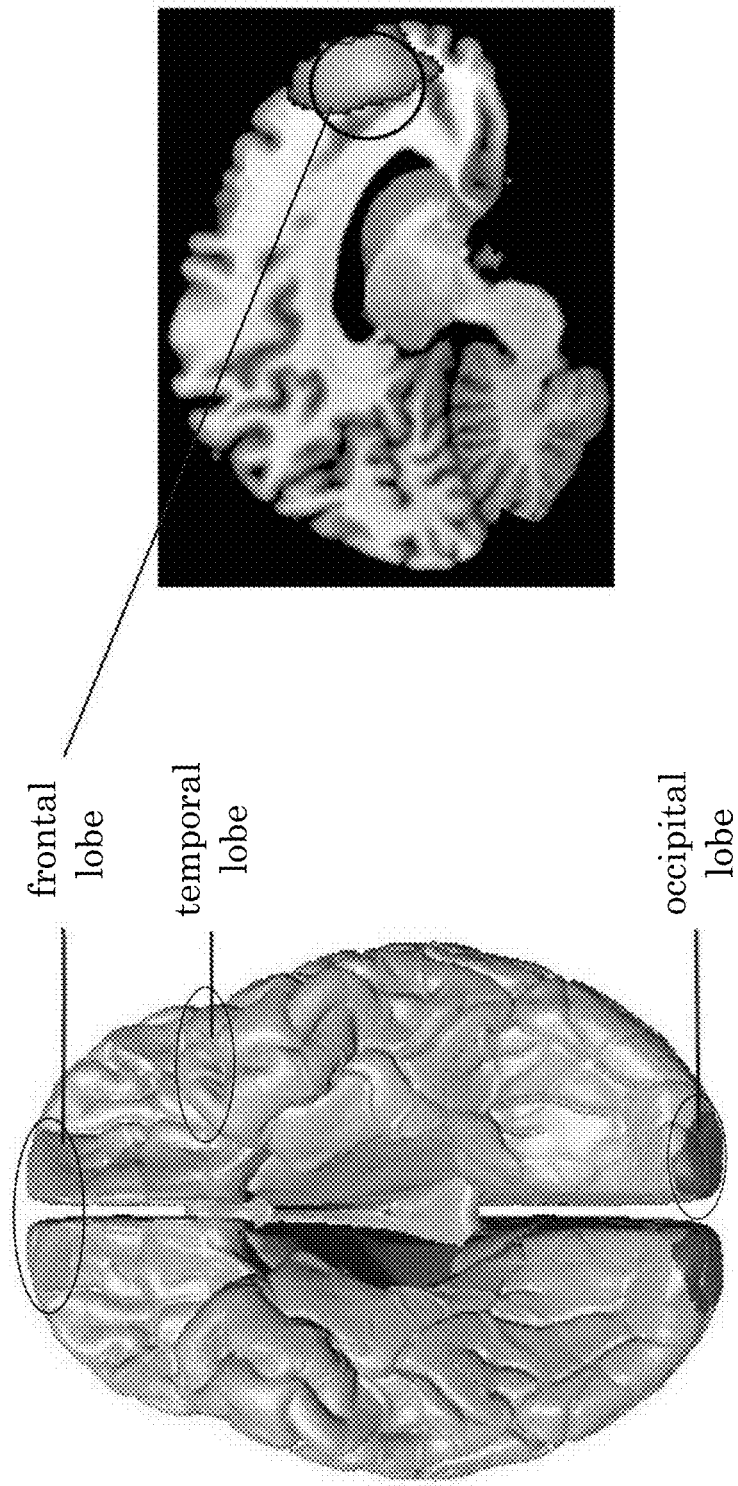
FIG. 2A is a diagram of the cerebrum viewed from below.
FIG. 2B is a diagram of the brain viewed from the left side plane.

FIGS. 2A and 2B are diagrams showing the position of the frontal pole in the appearance of the brain.

FIG. 2A is a diagram of the cerebrum viewed from below, and FIG. 2B is a diagram of the brain viewed from the left side plane.

As shown in FIGS. 2A and 2B, the frontal pole means the most forward portion of the cerebrum. This is a part of the prefrontal cortex, and corresponds to the most forward portion of the frontal lobe.

In the anatomical image, the gray matter volume (GM value) of the frontal pole of a test subject is evaluated.

The gray matter means a site of the nerve tissue of the central nervous system where the soma of the nerve cell exists. In the MRI image, when a T2 (transverse relaxation time) weighted image is used as the anatomical image, the gray matter shows a high signal level compared to the white matter.

The Voxel-Based-Morphometry (VBM) can be used for evaluating the volume of the gray matter, but not limited thereto.

The VBM is a method for calculating the difference in volume or tissue density among each limited area of the whole brain by the structural MRI, without being influenced by the skill level of a tester. Such a VBM is disclosed in the following literature, for example.

Known Literature 1: John Ashburner and Karl J. Friston, Voxel-Based Morphometry—The Methods, Neuroimage 11, 805, 2000.

In this technique, the MRI data adapted to the MNI standard brain is statistically evaluated in units of a voxel. Furthermore, an optimization method described in the following literature has been used recently.

Known Literature 2: Catriona D. Good et al., A Voxel-Based Morphometric Study of Ageing in 465 Normal Adult Human Brains, NeuroImage 14, 21-36 2001.

In this method, the anatomic standardization is performed using a customized template and a parameter unique to the gray matter.

On the other hand, in the diffusion weighted image, the diffusion anisotropy degree (FA value) of the test subject is evaluated.

In the following, the diffusion weighted image and the diffusion anisotropy degree will be briefly described.

(Diffusion Weighted Image and Diffusion Tensor)

The brain has a difference in the diffusibility of water (diffusion anisotropy) depending on the direction of the white matter fiber. Thanks to MRI, it is possible to quantitatively measure the degree of the diffusion anisotropy, mainly depending in the white matter fiber, by imaging meeting a certain condition and the tensor analysis.

The certain condition, to be explained briefly, corresponds to the acquisition of signals which appear after strong gradient magnetic fields are applied in the positive and negative directions, with respect to a certain direction for the above described gradient magnetic field. As for a stationary hydrogen atom, if the magnitudes of the positive and negative gradient magnetic fields are the same, the phase does not change. For example, if the gradient magnetic field in the X direction is changed as described above, the phase change occurs while the hydrogen atom is moving in the X direction, and thus detected as a signal. The level of the total signal is low in a voxel where many hydrogen nucleuses are violently diffusing in the X direction, whereas the total signal is strong in a voxel where many hydrogen nucleuses are hardly moving in the X direction. The gradient magnetic field to be applied for detecting the diffusion of hydrogen atoms is called a diffusion motion probing gradient (MPG) magnetic field.

In the measurement of the isotropic diffusion such as in an aqueous solution, the MPG only needs to be given in one direction, similarly to a conventional diffusion weighted image method. However, in an actual living body, the isotropic diffusion is impossible. Assuming that a certain voxel is the origin, when substances present at the origin diffuse in accordance with the Gaussian distribution, they are considered to be present in a region to be expressed as an ellipsoid after a certain amount of time. Hence, for dealing with the diffusion anisotropy quantitatively, the concept of the "diffusion tensor" is introduced. The diffusion tensor will be explained as follows.

$$D = \begin{pmatrix} D_{xx} & D_{yx} & D_{zx} \\ D_{xy} & D_{yy} & D_{zy} \\ D_{xz} & D_{yz} & D_{zz} \end{pmatrix} \quad \text{[Formula 1]}$$

where $D_{xy} = D_{yx}, D_{yz} = D_{zy}, D_{zx} = D_{xz}$

The diffusion tensor is a symmetric matrix having six independent elements.

Each of the elements of the diffusion tensor corresponds to an apparent diffusion coefficient (ADC) when the MPG is applied in the directions of the suffixes.

The MPG is applied in at least six directions, and the corresponding MRI images are acquired. Therewith, an image when the MPG is not applied, that is, the T2 weighted image is acquired. The difference from the T2 weighted image with no MPG application indicates the degree of the diffusion.

From the images when the MPG is applied in at least six directions, it is possible to calculate the diffusion tensor for each voxel.

The diagonalization is performed for the diffusion tensor. Thus, the principal directions of the orthogonal basic axes of the diffusion tensor are obtained as the corresponding eigenvectors, and the diffusion coefficients in the principal directions as the corresponding eigenvalues.

If the three eigenvalues are $\lambda_1$, $\lambda_2$ and $\lambda_3$, the above described diffusion anisotropy degree (FA value) is represented by the following formula.

$$FA = \sqrt{\frac{3}{2} \frac{\Sigma(\lambda_i - D_{av})^2}{\Sigma \lambda_i^2}} \quad \text{[Formula 2]}$$

$$D_{av} = \frac{\lambda_1 + \lambda_2 + \lambda_3}{3}$$

The FA value, which is a value of 0 to 1, is small when the diffusion anisotropy is small, whereas the FA value approaches 1 as the diffusion anisotropy increases.

The change in the FA value is considered to reflect the qualitative and quantitative change of the white matter fiber.

For a learner to utilize the "tendency discrimination device" and the "learning assisting device" according to the embodiment, the gray matter volume and FA value for the frontal pole of the learner are measured in advance by the MRI device 10 shown in FIG. 1.

(System Configuration)

In the following, the description will be made taking a foreign language for a learning theme of a learner as an example.

Further, the learning assisting device operates based on the discrimination result obtained by the tendency discrimination device, and thus, the learning assisting device will be described below. When the operation of the learning assisting device is implemented in software, the description will be made assuming that the function as the tendency discrimination device is incorporated as a part of the function of the software, but not limited thereto.

However, the tendency discrimination device may operate independently.

Figure 3:
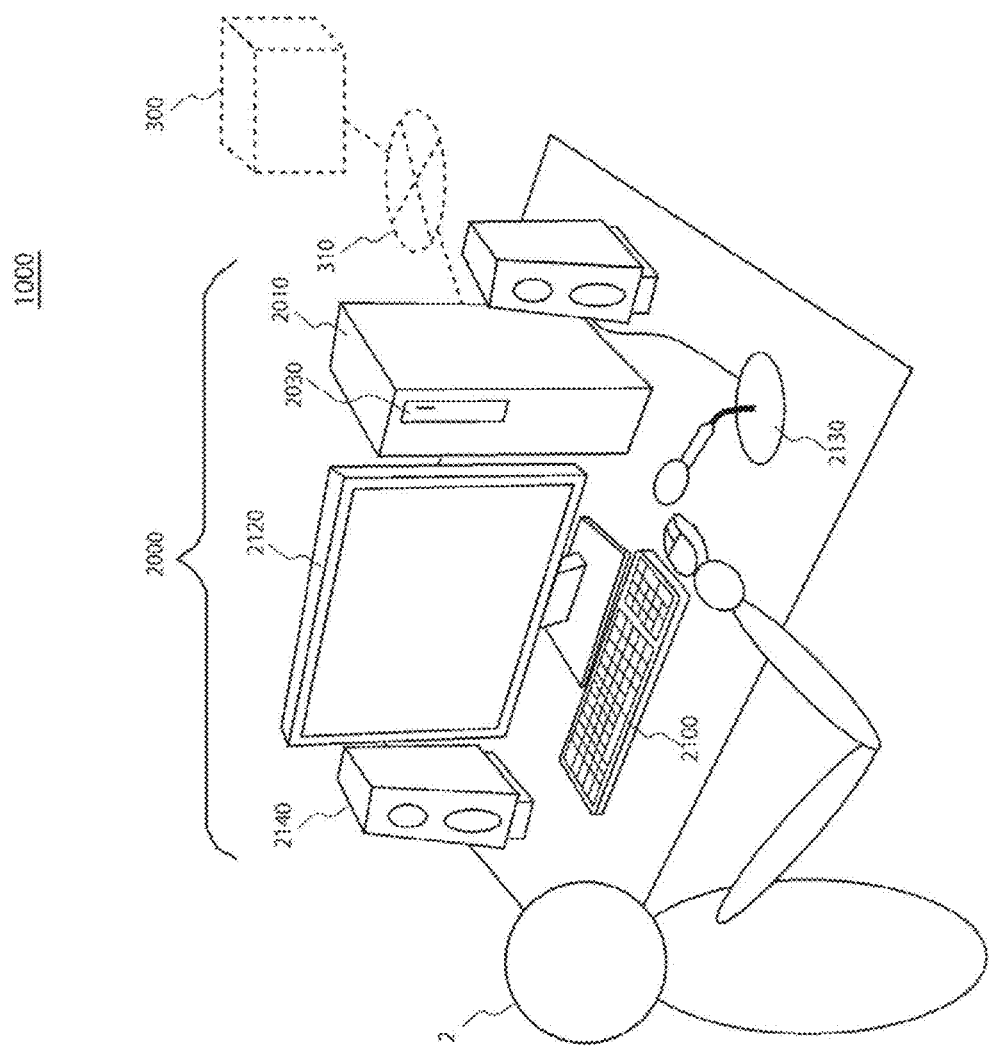
FIG. 3 is a conceptual diagram showing an exemplary system configuring a learning assisting device 1000.

FIG. 3 is a conceptual diagram showing an exemplary system configuring such a learning assisting device 1000.

With reference to FIG. 3, the learning assisting device 1000 includes a computer system 2000 for executing a process of sequentially presenting learning assignments at a certain step to a learner 2, the computer system 2000 providing the training program at the step to the learner or further presenting learning assignments at the next step to the learner based on the answers to the assignments from the learner.

The computer system 2000 includes a computer body 2010 having a disk drive 2030 for reading the information on a recording medium such as a compact disc read-only memory (CD-ROM), a display 2120 as a display device connected with the computer body 2010, a keyboard 2100 and a mouse 2110 as input devices connected with the computer body 2010, a microphone 2130 as a voice input device, and a speaker 2140 as a voice output device.

In some cases, the computer body can be connected with an external server 300 through a network 310, functioning as a client machine.

Figure 4:
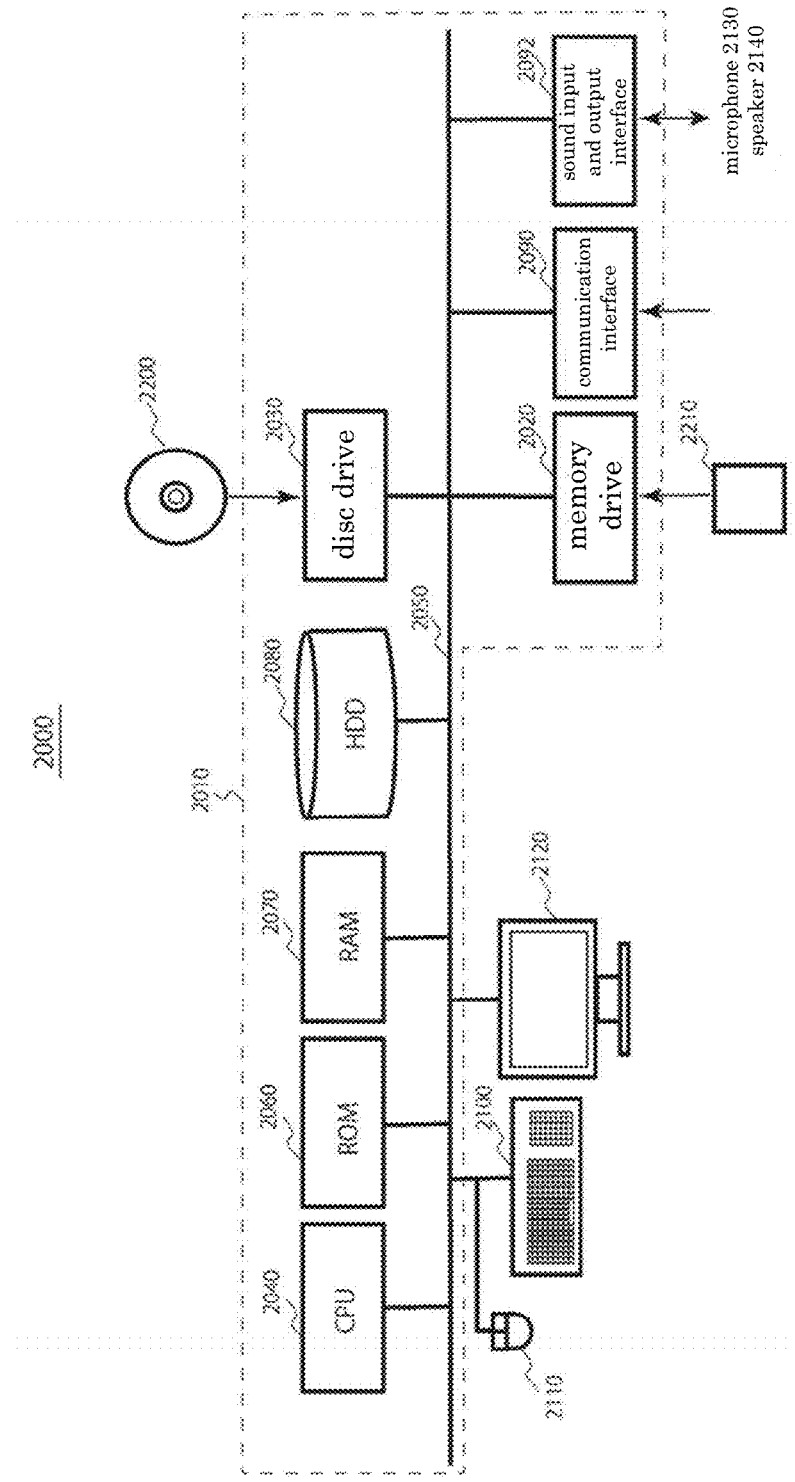
FIG. 4 is a diagram showing the hardware configuration of a computer system 2000 in the form of a block diagram.

FIG. 4 is a diagram showing the hardware configuration of the computer system 2000 in the form of a block diagram.

As shown in FIG. 4, the computer body 2010 constituting the computer system 2000 includes, in addition to the disk drive 2030 and a memory drive 2020, a central processing unit (CPU) 2040, a memory including a read only memory (ROM) 2060 and a random access memory (RAM) 2070, a rewritable non-volatile storage device such as a hard disk 2080, a communication interface 2090 for performing communication through a network, and a voice input/output interface 2092 for performing data exchange with the microphone 2130 or the speaker 2140, each of which is connected with a bus 2050. In the disk drive 2030, an optical disk such as a CD-ROM 2200 is mounted. In the memory drive 2020, a memory card 2210 is mounted.

As described below, the description will be made assuming that a database for containing the information as the basis of the operation is stored in the hard disk 2080 in case of operation of the program of the learning assisting device.

Here, in FIG. 4, the CD-ROM 2200 is a non-transitory medium capable of recording the information such as the program to be installed in the computer body. However, it may be another medium, for example, a DVD-ROM (Digital Versatile Disc). It may also be a memory card or a USB memory. In this case, drive devices capable of reading these media are provided in the computer body 2200.

The principal part of the learning assisting device 1000 is constituted by the computer hardware and the software executed by the CPU 2040. Typically, such software is stored in a storage medium such as the CD-ROM 2200 so as to be distributed, is read from the storage medium by the disk drive 2030 or so, and is temporarily stored in the hard disk 2080. Alternatively, when the device is connected with the network 310, it is temporarily copied from a server on the network to the hard disk 2080. Then, it is further loaded from the hard disk 2080 to the RAM 2070 of the memory, and is executed by the CPU 2040. In the case of being connected with the network, it may be directly loaded into the RAM and be executed, without being stored in the hard disk 2080.

The program for functioning as the learning assisting device 1000 does not necessarily need to include an operating system (OS) for making the computer body 2010 function as an information processing device or so. The program only needs to include just a command part for calling an appropriate function (module) in a controlled manner and obtaining an intended result. The detailed description about how the computer system 20 operates will be omitted because it is considered well known.

The computer for executing the above program may be a single computer, or may be plurality of computers. In other words, centralized processing may be performed, or distributed processing may be performed.

Moreover, the CPU 2040 may be a single processor, or may be plurality of processors. In other words, it may be a single-core processor, or may be a multi-core processor.

The database for containing the information as the basis of the operation of the program of the learning assisting device may be stored in an external storage device connected through the interface 2090. For example, in the case of being connected with the server 300 through the network 310 as shown in FIG. 3, the database for containing the information as the basis of the operation may be stored in a storage device such as a hard disk (not shown in the figure) in the server 300. In this case, the computer 2000 operates as a client machine, and exchanges the data in the database with the server 300 through the network 310. In addition, the computer 2000 may receive the data of assignments to be given to the learner from the server 300, display this, and return the data of the answer to the server.

Figure 5:
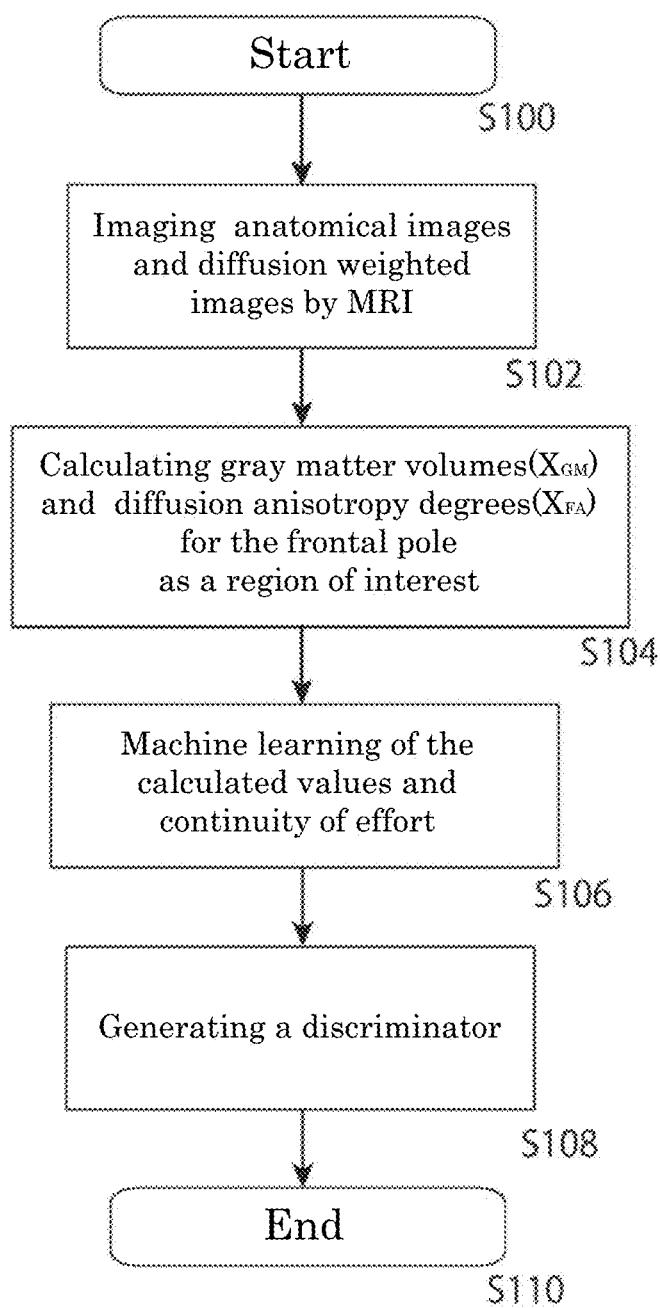
FIG. 5 is a flowchart for explaining a procedure for generating a "discriminator" to be used in a tendency discrimination device.

FIG. 5 is a flowchart for explaining a procedure for generating a "discriminator" to be used in the tendency discrimination device, which is included in a part of the program to function as the learning assisting device 1000.

The MRI measurement for the brain is performed by the MRI device 10 described in FIG. 1. Basically, the discriminator has been generated in advance by a computer having a configuration similar to described in FIG. 4. The information about such a discriminator may be incorporated in the program for functioning as the learning assisting device 1000, or may be configured to be appropriately updated from the server 300.

In the generation of the discriminator, first, a test is carried out in advance for a predetermined number or more of test subjects to discriminate their tendencies, by their cooperation.

As such a test, the test subjects work an assignment as a decision object, for example, a puzzle called the "tower of Hanoi", and whether they were finally able to solve it is recorded as information, for each test subject. The tower of Hanoi is a puzzle having the following rule.

For completion, all disks are moved to a right-end post, in accordance with the following rule.

i) This is configured by three posts, and plurality of disks having holes opened at the center and having different sizes.

ii) At first, all disks are piled at a left-end post in such an order that a smaller one is at an upper position.

iii) One disk can be moved to any post at one time, but a larger disk cannot be put on a smaller disk.

For moving all of n pieces of disks, at least $(2n-1)$ processes are required.

Therefore, whether to finally solve such a puzzle is considered to be one criterion for the judgment of a temperament about whether a test subject achieves an assignment or gives up on the way (referred to as the "continuity of effort").

Hence, the test result for each test subject is classified into "achieved the assignment" or "gave up". The classified results are stored in a storage device of a computer for discriminator generation, in association with the test subject.

With reference to FIG. 5, the MRI device 10 captures the anatomical image and the diffusion weighted image of the plurality of test subjects having taken the test described above (S102).

The data of the anatomical image and the diffusion weighted image are also stored in the storage device of the computer for generating the discriminator, in association with the test subjects.

Subsequently, in accordance with the above described procedure, the image processing unit 48 and the control unit 42 of the MRI device 10 calculates a gray matter volume XGM and a diffusion anisotropy degree XFA of the frontal pole as the region of interest, for the plurality of test subjects having taken the test described above (S104).

The CPU of the computer for generating the discriminator executes a process for the machine learning about the relationship of the gray matter volume XGM and diffusion anisotropy degree XFA calculated in this way to the continuity of the effort for an assignment (S106).

As the result of the process for such a machine learning, the discriminator is generated, and the information for configuring the discriminator is stored in the storage device (the hard disk 2080) (S108).

Instead of learning assisting device 1000 executing the process, another computer may execute the process for generating the discriminator, and the learning assisting device 1000 utilizes the information for configuring the discriminator generated in this way.

As for the machine learning, a so-called discriminant analysis can be used, but not limited thereto.

As for the discriminant function used for the discriminant analysis, there are the linear discriminant function with a hyperplane and a straight line, and the non-linear discriminant function of the Mahalanobis' generalized distance with a hypersurface and a curved line.

In the embodiment, as described above, the "continuity of effort" is classified into two groups. More typically, it can be classified into three or more groups, and this is called a plurality of discriminant analysis or a canonical discriminant analysis.

The classification into three or more groups, for example, may be performed by the combination of the successes and failures for plurality of assignments such as plurality of puzzles (for example, puzzles necessarily solvable even though it takes a long time is selected), based on whether the assignments are achieved.

Figure 6:
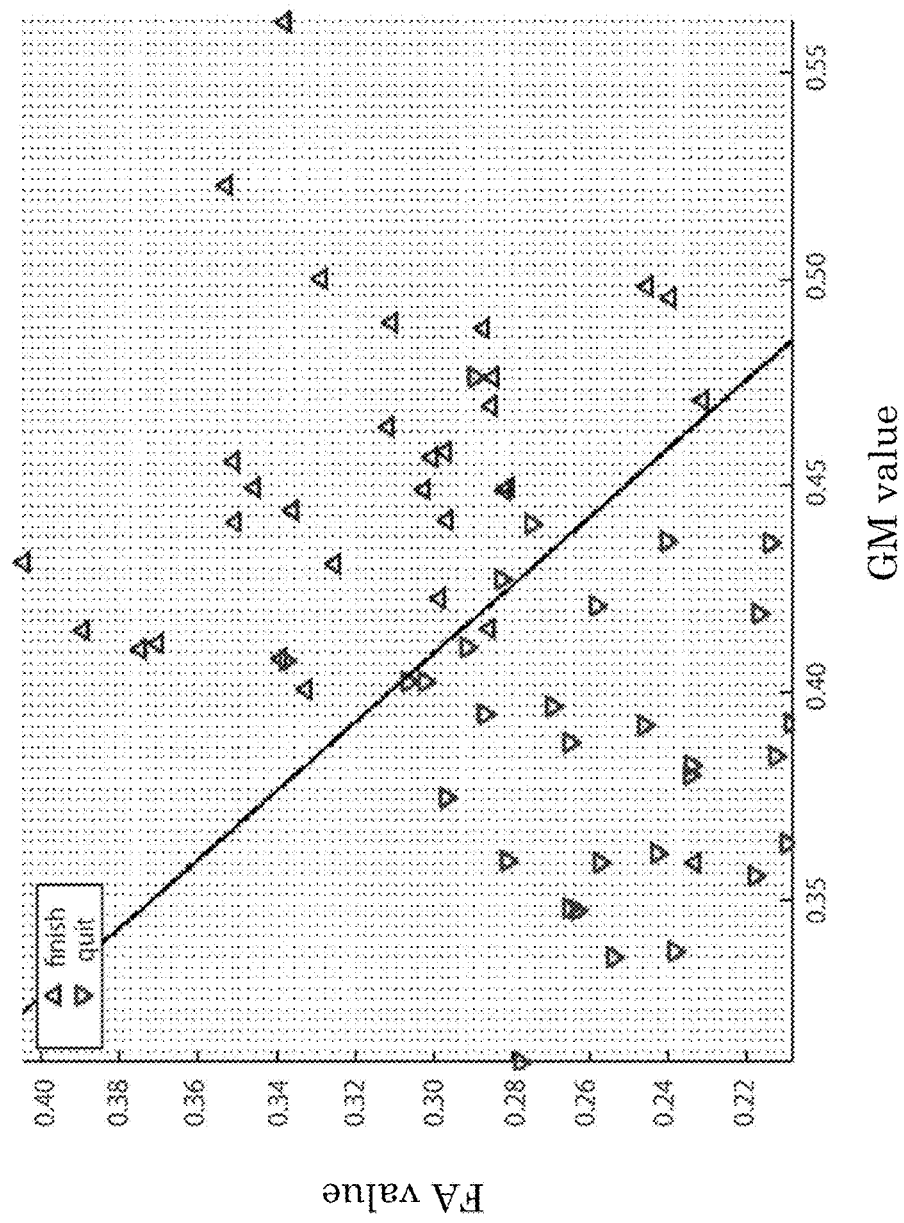
FIG. 6 is a diagram for explaining a situation of the discrimination by the discriminator.

FIG. 6 is a diagram for explaining a situation of the discrimination by the discriminator generated in this way.

In FIG. 6, the discriminant formula generated by the procedure described in FIG. 5 discriminates a test subject as a person having achieved the assignment of the "tower of Hanoi" or a person having given up on the way by using the GM value and FA value measured before the start of the learning. In the figure, a test subject marked with "finish" is a person having achieved the assignment, and a test subject marked with "quit" is a person having given up on the way. As shown in FIG. 6, the discrimination between the achievement and the give-up can be achieved with a probability of 80% or more.

The discriminator outputs the result of the discrimination as an "index of the tendency (to achieve an assignment requiring sustainability)".

By using such a discriminator, the discrimination of the potentiality as to whether to achieve the assignment of the "tower of Hanoi" can be performed, for a person to be tested having not yet taken the assignment.

Figure 7:
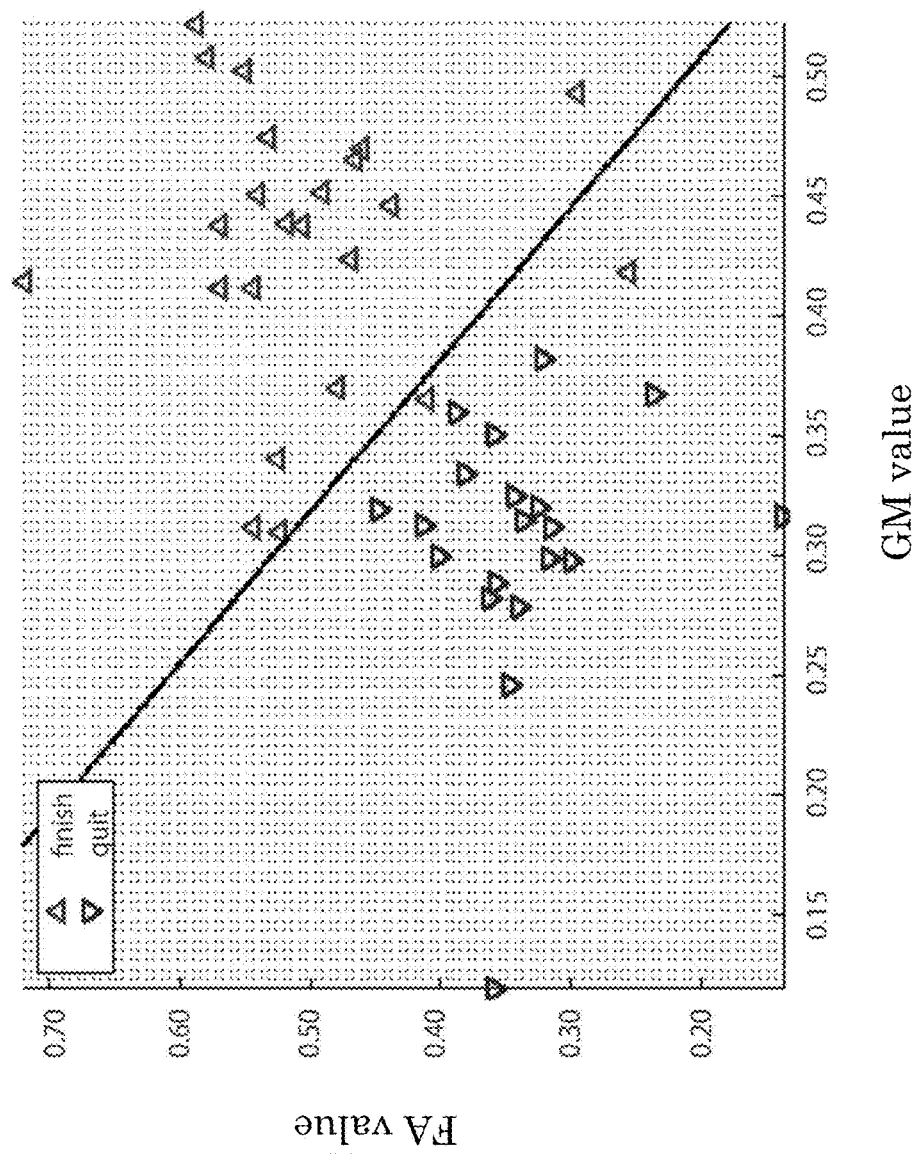
FIG. 7 is a different diagram for explaining a situation of the discrimination by the discriminator.

FIG. 7 is a different diagram for explaining a situation of the discrimination by the generated discriminator.

In FIG. 7, the discriminant formula generated by the procedure described in FIG. 5 discriminates a test subject as a person having achieved a four-month English learning actually or a person having given up on the way, by using the GM value and FA value measured before the start of the learning.

Similarly to the case of FIG. 6, by using this discriminator shown in FIG. 7, the discrimination of the potentiality as to whether to achieve the assignment of the "English learning" can be performed, for a person to be tested having not yet taken the assignment.

The discriminator outputs the result of the discrimination as an "index of the tendency (for learning)".

Figure 8:
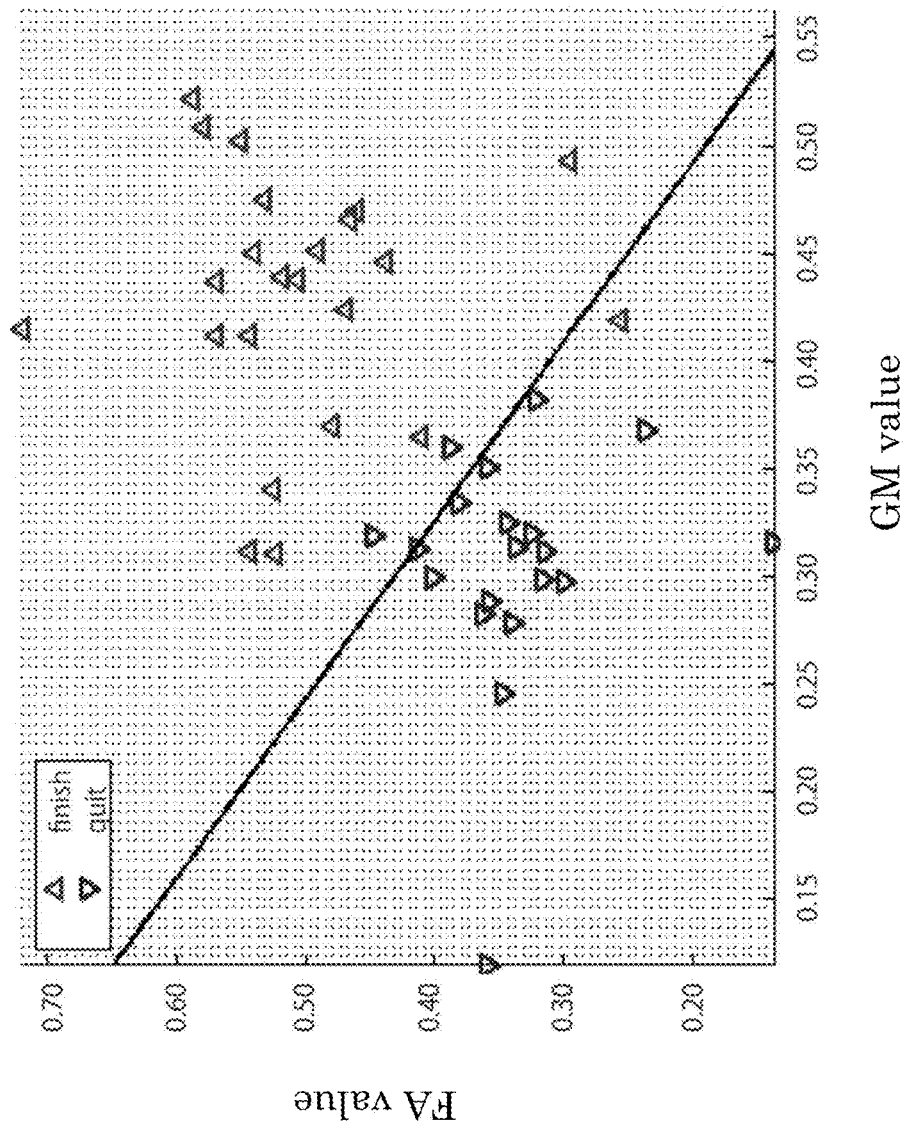
FIG. 8 is a further different diagram for explaining a situation of the discrimination by the discriminator.

FIG. 8 is a further different diagram for explaining a situation of the discrimination by the generated discriminator.

Here, the test subjects in FIG. 6 are different from the test subjects in FIG. 8, except a few persons.

FIG. 8 shows the case of discriminating whether the English learning could be achieved, with the discriminator generated in the tower of Hanoi. The discriminator itself is the same as the discriminator shown in FIG. 6. That is, unlike the cases in FIG. 6 and FIG. 7, in which the potentiality of the achievement is discriminated by the discriminator generated in the same different assignment, the discriminator generated in the "tower of Hanoi" can be used for the discrimination of whether to achieve, within the predetermined period of time, the learning program of the "English learning" composed by a predetermined assignment unit, which is different from the assignment for generating the discriminator.

That is, the verification using the different test subject groups reveals that there is no difference between the tendency to achieve an assignment in a short-period assignment such as the "tower of Hanoi" and the tendency to achieve a sustainability-requiring assignment in a long-period assignment such as the English learning. In other words, the tendency discriminated here is a "common tendency in terms of the 'achievement of an assignment', which does not depend on the time needed to achieve the assignment and on the content of the assignment".

This shows that the tendency extracted by the "continuity of effort" for the assignment of the "tower of Hanoi" can be an "index of the tendency to achieve a sustainability-requiring assignment" such as the "English learning".

In this case, the discriminator also outputs the result of such a discrimination as an "index of the tendency (for learning)".

Figure 9:
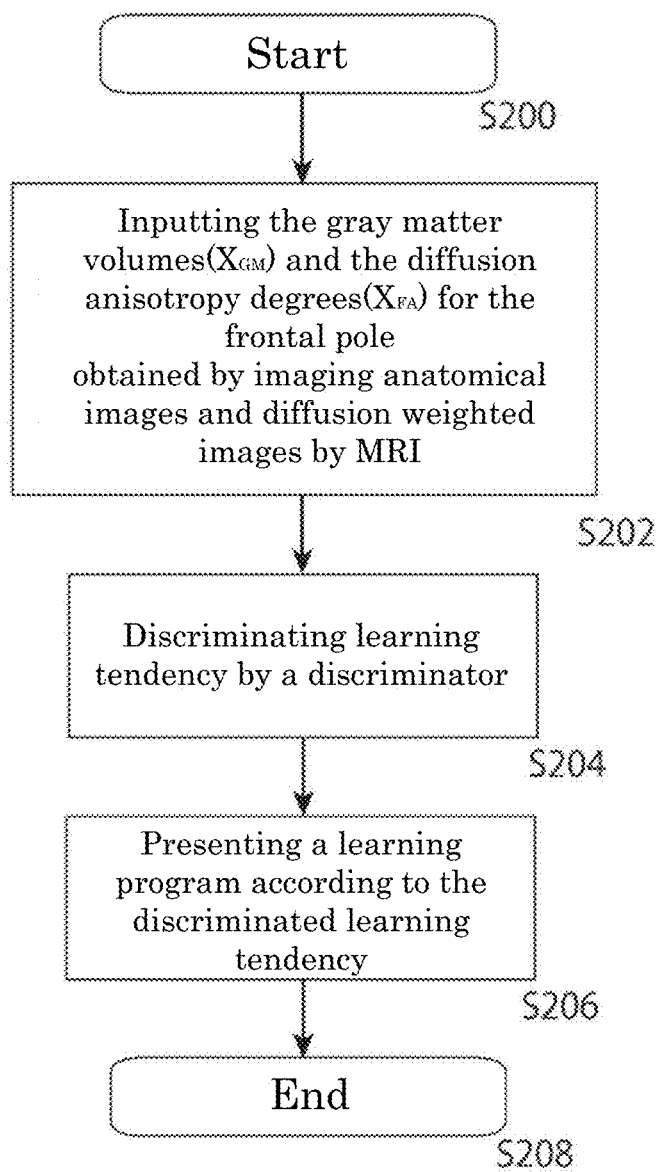
FIG. 9 is a diagram for explaining a procedure of the learning assistance by the learning assisting device 1000.

FIG. 9 is a diagram for explaining a procedure of the learning assistance by the learning assisting device 1000.

Similarly to the above description, the imaging of the anatomical image and the diffusion weighted image is previously obtained for a learner by the MRI device 10, and the gray matter volume XGM and the diffusion anisotropy degree XFA are previously calculated for the frontal pole of each test subject as the region of interest.

The learning assisting device 1000 receives the calculated gray matter volume XGM and anisotropy degree XFA as an input (S202), and then, discriminates the tendency of the learner by the discriminant formula described above (S204).

The learning assisting device 1000 presents a learning program more appropriate for the learner, in response to the index of the discriminated tendency (S206). On this occasion, as described above, the learning assisting device 1000 may execute the process of sequentially presenting learning assignments of a certain step to the learner 2, and then the process of further providing, based on the answers to the assignments from the learner, the training of the current step or learning assignments of the next step to the learner.

Here, for example, it is possible to previously input the information such as the fields of the hobbies and jobs of learners to the system, and to add variety to an assignment given to a learner discriminated as "there is a tendency to give up on the way" as the index of the tendency, for example, by putting many topics associated with such fields, in the themes in a foreign language as the learning object.

Alternatively, it is also possible to adjust the combination of the categories (listening, reading, speaking, words, and grammar) and others of the assignments, or the frequency of the switching among those categories.

Further, if the index of the tendency has been classified into plurality of groups, it may previously perform the corresponding of plurality of levels different in the ratio of putting topics in interesting fields or plurality of levels different in the frequency of the category switching, to the groups for the index of the tendency, in the learning program. The "plurality of groups for the index of the tendency", for example, may be not only groups for the strength of the degree of a particular tendency, but also groups classified in a way where plurality of tendencies are considered in combination and where each of the plurality of tendencies corresponds to each dimension.

If the learning object is not a foreign language, it is possible to present assignments according to the index of the tendency and to perform a similar process to a foreign language, by classifying the field of each assignment in association with the interest of the learner to increase or decrease the ratio of the assignment of an interesting field in the progress of the learning program, or by previously classifying the category of the assignment to increase or decrease the frequency of the switching of the category of the assignment. For example, for a learner having a high tendency to give up an assignment on the way as the index of the tendency, it is possible to increase assignments in an interesting field, or to increase the frequency of the switching of the category. Such a corresponding between the ratios of the assignments or the frequencies of the switching and the levels of the tendency is not limited thereto. For example, the corresponding can be performed by experimentally examining, for many test subjects in advance, the relationship between the level of the tendency discriminated by the tendency discrimination device, and whether the ratio of test subjects able to achieve the learning increases to a predetermined value or more.

In this specification, the description "switching of the mode of the presentation of the assignment" refers to switching of kinds or providing ways of the assignment given to a person to be tested depending on the tendency of the person discriminated by using the discrimination result obtained from the tendency discrimination device, and includes a switching of the assignment itself.

As for the kind and proving way of the assignment given to the learner, for example, the following is also possible.

i) Reward Giving Learning. An extrinsic reward (money or grade evaluation) in accordance with the reward sensitivity of an individual is given. The reward sensitivity of the individual is measured, the extrinsic reward is given based on the learning quantity, and thereby, the learning continuation is encouraged.

ii) Successful Experience Giving Learning. Minute learning goals each of which is relatively easy to achieve are set, and thereby, successful experiences (intrinsic rewards) are given. Thereby, the learning continuation is encouraged. In the method, in the case of a learning including plurality of grades as a whole, for example, 50 grades are divided in units of 5 grades or the like, and whenever 5 grades are completed, the evaluation of the assignment success is presented to the learner.

iii) Transcranial Magnetic Stimulation (TMS), Transcranial Direct Current Stimulation (tDCS). By a neurofeedback training, the brain function activity is extrinsically changed. Thereby, the learning continuation is encouraged.

As for the intrinsic reward, for example, the achievement degree may be clearly shown by scoring. Further, after a certain period of time, the index of the gray matter quantity or the white matter anisotropy may be fed back to the learner. Alternatively, for a learner overly persisting in the success of one assignment and having little flexibility, the providing way of the assignment may be altered, such as by forcing the learner to deal with an assignment shift or so, depending on the time spent on the assignment by the learner.

In the above description, the "tendency" has been described, taking as examples the "tendency" for a task requiring the sustained work, such as the "tower of Hanoi", and the "learning tendency" for a long-period task, such as the learning of English. However, the term "index of tendency", more generally, can also include the "index of the tendency for the behavior sustainability" for a theme requiring the sustaining of a continuous and repetitive task (assignment) for a certain period of time, such as smoking cessation and dieting. In this case, the task execution assisting device can present an attainment assignment content, an attainment time, and the like, for a behavior program that should be performed by a user executing the "smoking cessation" or the "dieting", depending on the index of the tendency. "Behavior programs that should be performed by a user" for these purposes, such as education or health promotion, are collectively referred to as "task programs".

The "tendency" may include the "index of the tendency of a disease" for the person to be tested relevant to a mental disease (for example, depression) or a psycho-neurologic disease. In this case, for example, the task execution assisting device can present an attainment assignment content, an attainment time, and the like, for a program such as "social skill training", to a trainer or so, depending on the index of the tendency. Then, the "task program" may include such a "training program" for a therapeutic purpose.

Such a configuration enables the tendency discrimination device according to the embodiment to objectively discriminate the tendency of a person to be tested, from the MRI measurement data for the brains of the test subjects.

Further, the task execution assisting device can objectively discriminate the tendency of a test subject, from the MRI measurement data for the brains of the test subjects, and can provide an execution program appropriate for the test subject.

(Experiment about Motor Learning)

In the following, results for the discrimination of learner's tendency will be described when the tendency discrimination device described above is applied to a "motor learning", other than the foreign language learning.

(Content of Motor Learning)

Figure 10:
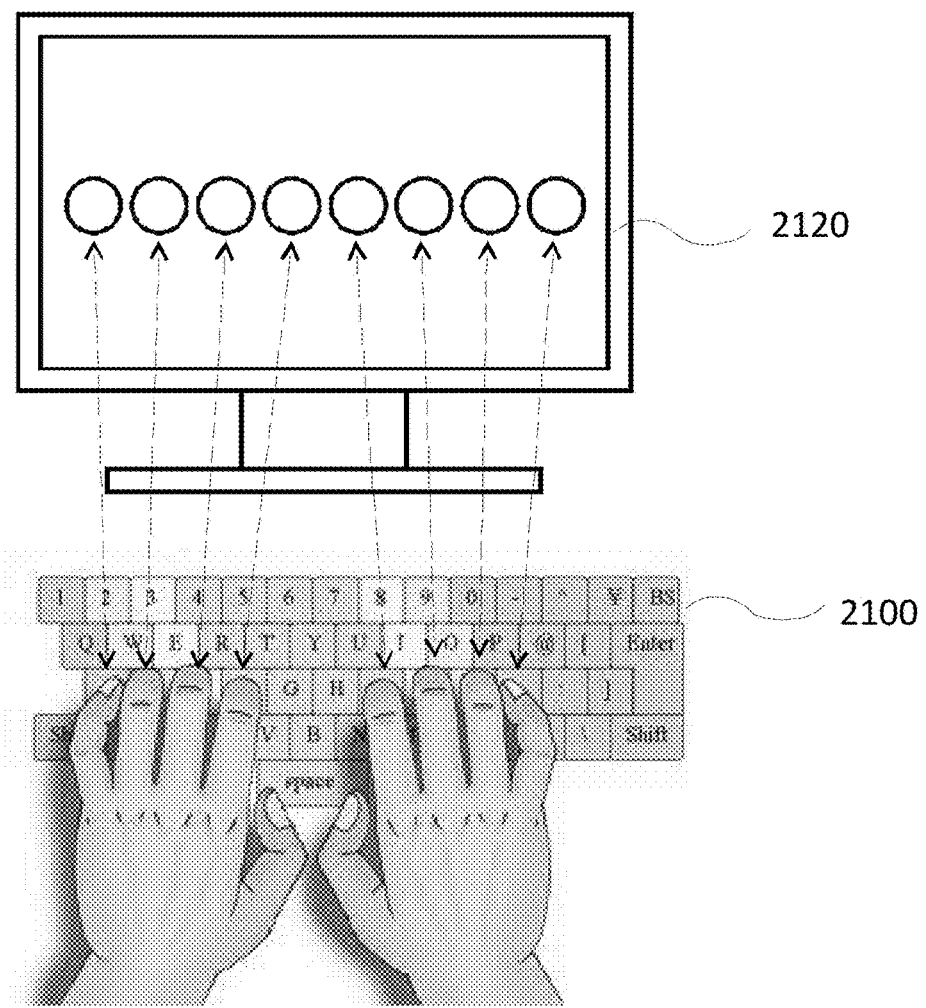
FIG. 10 is a conceptual diagram for explaining the content of a motor learning.

FIG. 10 is a conceptual diagram for explaining the content of a motor learning.

For a learning content described below, each learner executed e-learning program daily for a month.

In the learning, as shown in FIG. 10, eight circles are always presented on the screen of the display 2120, and the circles correspond to predetermined PC keyboard 2100 and predetermined fingers. That is, each of the little finger of the left hand, the third finger, . . . , the index finger of the right hand, the middle finger, . . . , the little finger of the right hand, which are the fingers except the thumbs, corresponds to a key to be typed with it and the circle mark on the screen.

As described below, the learner finds out a hidden proper order of sequentially typing the keys through the learning.

That is, once the learner presses a key corresponding to a circle mark on the screen, a hit/error indicator is displayed at the position of the circle mark on the screen each time. By repeating trial and error in daily learning, the learner finds out the hidden sequence (the proper order for pressing the keys ten times) by using the hit/error indicator as a clue, and memorizes the sequence. When the learner comes to be able to type in the proper sequence in tune with a sound of 2 Hz, the learning of the day finishes.

In this way, a sequence of a 10-time typing is memorized in a day, and the proper sequence to be memorized is set to become longer day by day.

For example, the first day's learning is a typing sequence of a 10-time typing, and the second day's typing is a typing sequence of a new 10-time typing in addition to the first day's 10-time typing. Thus, the number of key typing of the correct answer is increased day by day. If the learner can learn the order of a 50-time typing in a week, and if, eventually after a month, can perform a 200-time key typing in a proper sequence in tune with a sound of 2 Hz, the learner succeed.

The learner had to retry it from the first typing when failing in the type, even though it was the 199-th.

(Result of Motor Learning)

Such a motor learning was performed by 41 persons. As a result, 22 persons achieved, and 19 persons gave up.

Meanwhile, a discriminant analysis by using the "discriminator generated for the tendency whether to achieve a short-period assignment" described above could predict a behavior result for achievement or give-up in the motor learning with a probability of 80%.

From the result, it can be said that the discriminator according to the embodiment can discriminate a general tendency to complete an assignment without depending on the assignment content (such as a language learning, a motor learning, a long-period task, or a short-period task).

Furthermore, in the above motor learning, whether the ratio of successful learners changes depending on the mode of the presentation of the assignment was confirmed by the following experiment.

i) The discrimination by the above described discriminator was performed in advance for a predetermined number of test subjects.

ii) Then, the test subjects were divided at random into two groups as follows:

First group: a total of 40 persons . . . a group in which half (20 persons) of them are test subjects discriminated as "give-up"

Second group: a total of 41 persons . . . a group in which half (20 persons) of them are test subjects discriminated as "give-up"

iii) The learners of the first group executed the above described learning assignment exactly. For the learners of the second group, in the execution of the above motor learning, whenever the learner achieves a small segment (one segment was a 3 to 5-time typing), the learner was given a sense of achievement with the display of "Clear" as a goal achievement presentation.

As a result, in the first group, 18 persons of the 20 persons predicted as "give-up" quit. On the other hand, in the second group, 16 persons of the 20 persons predicted as "give-up" achieved.

From the result described above, it can be said that it is possible to increase the achievement rate for learning, by previously discriminating the tendency of the learner based on the discrimination result from the discriminator according to the embodiment, and by selecting the presentation mode of the assignment depending on the tendency of each learner.

The embodiment disclosed herein exemplifies configurations for specifically carrying out the present invention, and does not limit the technical scope of the present invention. The technical scope of the present invention is determined not by the description of the embodiment but by the claims, and include alterations within the literal range of the claims and the range of the equivalent meanings.

REFERENCE SIGNS LIST 2 test subject, 6 display, 10 MRI device, 11 magnetic field applying mechanism, 12 static magnetic field generating coil, 14 gradient magnetic field generating coil, 16 RF irradiating unit, 18 bed, 20 receiver coil, 21 drive unit, 22 static magnetic field power source, 24 gradient magnetic field power source, 26 signal transmitting unit, 28 signal receiving unit, 30 bed driving unit, 32 data processing unit, 36 storage unit, 38 display unit, 40 input unit, 42 control unit, 44 interface unit, 46 data collecting unit, 48 image processing unit, 2000 learning assisting device system, 2010 computer body, 2020 optical disk drive, 2030 optical disk drive, 2040 CPU, 2050 bus, 2060 ROM, 2070 RAM, 2080 hard disk, 2100 keyboard, 2110 mouse, 2120 display, 2210 memory card

What is claimed is:

1. A tendency discrimination device comprising:
   a non-transitory recording medium for storing
     data of an anatomical image and a diffusion weighted image, obtained by magnetic resonance imaging for each of a plurality of subjects, and
     classification information in association with each of the plurality of subjects, obtained by classifying results of an assignment undertaken by each of the plurality of subjects when given a test for judging a tendency; and
   a computer for executing a process for tendency discrimination, based on the data and the classification information stored in the storage unit, said process comprising
     calculating a gray matter volume and a diffusion anisotropy degree for a predetermined brain region of each of the plurality of subjects as a region of interest, based on the anatomical image and the diffusion weighted image, and
     generating a discriminator by a machine learning of relationship of the classification information to the gray matter volume and the diffusion anisotropy degree, wherein the discriminator outputs a tendency index of a person to be tested, wherein the discriminator discriminates the potential of the person to be tested of finishing an assignment of a program, which has not yet been taken by the person to be tested, based on the outputted tendency index, wherein the assignment of the program is different from the assignment undertaken by the subjects when given the test for judging.

2. A tendency discrimination device for discriminating a tendency of a person to be tested comprising:

a computer processor; and a memory storing a computer executable program which, when executed by the computer processor, performs the following, invoke operation of a discriminator which is generated by a machine learning of relationship of information obtained by classifying results of an assignment, which is undertaken by a plurality of subjects when given a test, to gray matter volumes of the plurality of subjects and diffusion anisotropy degrees of the plurality of subjects, the test being for judging tendencies of the plurality of subjects, the gray matter volumes and the diffusion anisotropy degrees being acquired for a predetermined brain region of each of the plurality of subjects as a region of interest, based on anatomical images and diffusion weighted images obtained by magnetic resonance imaging, output a tendency index of the person to be tested, which is determined by the discriminator from a gray matter volume of the person to be tested and a diffusion anisotropy degree of the person to be tested, the gray matter volume and the diffusion anisotropy degree being acquired for the predetermined brain region of the person to be tested as the region of interest, based on an anatomical image and a diffusion weighted image of the person to be tested obtained by magnetic resonance imaging, and use the outputted tendency index to discriminate the potential of the person to be tested of finishing an assignment of a program, which has not yet been taken by the person to be tested, wherein the assignment of the program is different from the assignment undertaken by the plurality of subjects when given the test for judging.

3. The tendency discrimination device according to claim 1, wherein the program is a task program, and the tendency index is an index relevant to behavior sustainability of the person to be tested.

4. The tendency discrimination device according to claim 3, wherein the predetermined brain region is a frontal pole.

5. The tendency discrimination device according to claim 1, wherein the program is a learning program, and the tendency index is an index relevant to a tendency of the person to be tested for learning.

6. A learning assisting device comprising:

a non-transitory recording medium for storing information about a discriminator generated by a machine learning of relationship of information obtained by classifying results of a test to gray matter volumes of a plurality of subjects and diffusion anisotropy degrees of the plurality of subjects, the test being for judging tendencies of the plurality of subjects, the gray matter volumes and the diffusion anisotropy degrees being for a predetermined brain region of each of the plurality of subjects as a region of interest, based on anatomical images and diffusion weighted images obtained by magnetic resonance imaging; and a computer processor; and a memory storing a computer executable program which, when executed by the computer processor, performs the following, invoke operation of the discriminator, and output a learning tendency index of a person to be tested, which is generated by the discriminator from a gray matter volume of the person to be tested and a diffusion anisotropy degree of the person to be tested, the gray matter volume and the diffusion anisotropy degree being acquired for the predetermined brain region of the person to be tested as the region of interest, based on an anatomical image and a diffusion weighted image of the person to be tested obtained by magnetic resonance imaging, and switching a presentation mode of presenting a ratio of categories of assignments in a program given to the person to be tested, and/or modifying a number of times of switching the categories of assignments presented in the program, depending on the learning tendency index, in such manner as to increase the potential of the person to be tested of achieving the assignments in the program.

7. The learning assisting device according to claim 6, wherein the program is a task program, and the learning tendency index is an index relevant to behavior sustainability of the person to be tested.

8. The learning assisting device according to claim 7, wherein the predetermined brain region is a frontal pole.

9. The learning assisting device according to claim 6, wherein the program is a learning program, and a field of each of the plurality of assignments of the learning program is classified in association with an interest of the person to be tested, or a category of each of the plurality of assignments is previously classified, and wherein, in progress of the learning program, a ratio of assignments in the classified field is increased or decreased, or a frequency of switching of the category of the assignments is increased or decreased, depending on the tendency index of the person to be tested.

10. A non-transitory computer readable medium on which is stored a tendency discrimination computer program which, when executed by a computer, causes the computer to:

acquire a gray matter volume for a predetermined region of a person to be tested and a diffusion anisotropy degree for the predetermined brain region of the person to be tested as a region of interest, based on an anatomical image and a diffusion weighted image obtained by magnetic resonance imaging; and output a learning tendency index for the region of interest of the person to be tested, based on a discriminant function generated by a machine learning of relationship of information obtained by classifying results of an assignment, which is undertaken by a plurality of subjects when given a test, to gray matter volumes of the plurality of subjects and diffusion anisotropy degrees of the plurality of subjects, the test being for judging tendencies of the plurality of subjects, the gray matter volumes and the diffusion anisotropy degrees being acquired for the predetermined brain region of the plurality of subjects as the region of interest based on anatomical images and diffusion weighted images obtained by magnetic resonance imaging; and use the outputted learning tendency index to discriminate the potential of the person to be tested of finishing an assignment of a learning program, which has not yet been taken by the person to be tested, wherein the assignment of the learning program is different from the assignment undertaken by the plurality of subjects when given the test for judging comprised.

11. A non-transitory computer readable medium on which is stored a learning assisting computer program which, when executed by a computer, causes the computer to:
   acquire a gray matter volume for a predetermined brain region of a person to be tested and a diffusion anisotropy degree for the predetermined brain region of the person to be tested as a region of interest, based on an anatomical image and a diffusion weighted image obtained by magnetic resonance imaging;
   output a learning tendency index of the person to be tested, based on a discriminant function generated by a machine learning of relationship of information obtained by classifying results of a test to gray matter volumes of a plurality of subjects and diffusion anisotropy degrees of the plurality of subjects, the test being for judging learning tendencies of the plurality of subjects, the gray matter volumes and the diffusion anisotropy degrees being acquired for the predetermined brain region of each of the plurality of subjects as the region of interest based on anatomical images and diffusion weighted images obtained by magnetic resonance imaging; and
   switch a ratio of categories of presenting assignments in the learning program given to the person to be tested, and/or modifying a number of times of switching the categories of assignments presented in the learning program, depending on the learning tendency index, in such manner as to increase the potential of the person to be tested of achieving the assignments in the learning program.

12. A learning assisting device comprising: a magnetic resonance imaging scanner for acquiring a gray matter volume for a predetermined brain region of a person to be tested and a diffusion anisotropy degree for the predetermined brain region of the person to be tested as a region of interest, based on an anatomical image and a diffusion weighted image obtained by magnetic resonance imaging; and a computer processor coupled with a memory storing a computer executable program which, when executed by the computer processor, switches a mode a ratio of categories of assignments in a learning program given to the person to be tested and/or modifies a number of times of switching the categories of assignments presented in the learning program depending on a learning tendency of the person to be tested in such manner as to increase the potential of the person to be tested of achieving the assignments in the learning program, the mode being a presentation mode of an assignment in a learning program given to the person to be tested, the learning tendency of the person to be tested being discriminated from the brain information of the person to be tested based on a discriminator, the discriminator being generated by a machine learning of relationship of information obtained by classifying results of a test to gray matter volumes of a plurality of subjects and diffusion anisotropy degrees of the plurality of subjects, the test being for judging learning tendencies of the plurality of subjects, the gray matter volumes and the diffusion anisotropy degrees being acquired for the predetermined brain region of each of the plurality of subjects as the region of interest based on anatomical images and diffusion weighted images obtained by magnetic resonance imaging.

13. The learning assisting device according to claim 12, wherein the computer processor, depending on the learning tendency of the person to be tested, switches a timing when giving an evaluation notice of assignment achievement degree of the person to be tested, in the learning program given to the person to be tested.

14. The tendency discrimination device according to claim 2, wherein the program is a task program, and the tendency index is an index relevant to behavior sustainability of the person to be tested.

15. The task execution assisting device according to claim 7,
   wherein a field of each of the plurality of assignments of the learning program is classified in association with an interest of the person to be tested, or a category of each of the plurality of assignments is previously classified, and
   wherein, in progress of the learning program, a ratio of assignments in the classified field is increased or decreased, or a frequency of switching of the category of the assignments is increased or decreased, depending on the tendency index of the person to be tested.

16. The learning assistance device according to claim 6, wherein the program is a learning program, and the tendency index is an index relevant to a tendency of the person to be tested for learning.

17. The tendency discrimination device according to claim 1, wherein the non-transitory recording medium comprises at least one of a Compact Disc Read-Only Memory (CD-ROM), a Digital Versatile Disc Read-Only Memory (DVD-ROM), a Universal Serial Bus (USB) memory, a memory card, and a hard disk.

18. The learning assistance device according to claim 6, wherein the non-transitory recording medium comprises at least one of a Compact Disc Read-Only Memory (CD-ROM), a Digital Versatile Disc Read-Only Memory (DVD-ROM), a Universal Serial Bus (USB) memory, a memory card, and a hard disk.

* * * * *